(12) United States Patent
Lee et al.

(10) Patent No.: US 6,253,629 B1
(45) Date of Patent: Jul. 3, 2001

(54) AUTOMATIC SAMPLING METHOD AND FACILITY FOR HETEROGENEOUS MATERIALS

(75) Inventors: Maw-Chwain Lee, Taipei; Yu-Tang Yang, Tao Yuan; Fun-Yeuan Hwang, Tao Yuan; Yuen-Liang Chen, Tao Yuan, all of (TW)

(73) Assignee: Institute of Nuclear Energy Research (TW)

( * ) Notice: Subject to any disclaimer, the term of this patent is extended or adjusted under 35 U.S.C. 154(b) by 0 days.

(21) Appl. No.: 09/399,763

(22) Filed: Sep. 21, 1999

(30) Foreign Application Priority Data

Apr. 13, 1999 (TW) .................................................. 88105822

(51) Int. Cl.$^7$ ...................................................... G01N 1/08
(52) U.S. Cl. ........................................................ 73/864.45
(58) Field of Search ........................... 73/864.42, 864.44, 73/864.45, 864.73, 864.74, 863.81, 863.82, 863.83

(56) References Cited

U.S. PATENT DOCUMENTS

| | | | |
|---|---|---|---|
| 3,206,981 | * | 9/1965 | Jameson ........................... 73/863.83 |
| 4,345,484 | * | 8/1982 | Gould et al. ...................... 73/864.44 |
| 5,211,062 | * | 5/1993 | Moser ............................... 73/863.83 |

FOREIGN PATENT DOCUMENTS

1375976 * 2/1988 (SU) .................................. 73/864.74

* cited by examiner

Primary Examiner—Robert Raevis
(74) Attorney, Agent, or Firm—Burns, Doane, Swecker & Mathis, L.L.P.

(57) ABSTRACT

An automatic sampling method and facility are disclosed, by means of which multiple samples are obtained from a closed container filled with heterogeneous solid material. The sampling points are predetermined and well distributed on the container and the sampling position and depth in the container are selected by a special controller of the sampling system. The system can be operated at an open space for non-radioactive material. The obtained samples are collected and blended in a mixer for homogenization treatment to produce a final specimen for analytical measurement. The homogeneous specimen is well accepted for its representative character.

10 Claims, 5 Drawing Sheets

AUTOMATIC SAMPLING METHOD AND FACILITY FOR HETEROGENEOUS MATERIALS

FIELD OF THE INVENTION

The present invention relates to a sampling method and facility for the heterogeneous solid materials and, more particularly, to an automatic sampling method and the necessary facility for sequential sampling of the heterogeneous solid materials.

BACKGROUND OF THE INVENTION

In early days, a large quantity of wet Ammonium Uranyl Tricarbonate (AUT) slurry was produced from the phosphoric acid plant in the Institute of Nuclear Energy Research (INER), Taiwan. Initially, the AUT slurry was packed in PVC tanks.

After storage for a long time, the aged PVC tanks were likely to deteriorate and break and any leakage of AUT would result in an environmental contamination. Hence, the AUT slurry was subjected to a batchwise calcination treatment and packed in new containers. The dried AUT powder or agglomerate owns diverse particle size and shape as well as the uranium content and in both physical property and chemical composition AUT are heterogeneous. The 55-gallon drum is the new container and after AUT packing, the weight of each drum is several hundred kilograms.

According to the agreements between Taiwan and the International Atomic Energy Agency (IAEA), the category and account of nuclear materials owned by a state must be well established. It is necessary to determine the exact quantity of uranium in AUT stock by sampling and reliable analytical method. However, a representative sample is not easily obtained due to the heterogeneous property of AUT unless a facility for AUT homogenization treatment by milling and blending is established. Furthermore, operation cost and facility investment are high for such an AUT homogenization system. In order to obtain an AUT sample well recognized by INER and IAEA, an invention of sampling method and facility with limited investment is developed. The uranium content of AUT is determined and the analytical results are well accepted by both organizations.

In addition to AUT, this technology can also provide an effective method for sampling of the heterogeneous solid materials, either powder or agglomerate, used in agricultural and industrial areas.

SUMMARY OF THE INVENTION

Accordingly, an object of the present invention is to provide a relatively simple and effective sampling method for heterogeneous solid materials. Multiple samples are obtained from a closed container filled with powder or agglomerate of a heterogeneous solid material. The sampling points are predetermined and well distributed on the container. The sampling position and depth in the container are selected by a special controller of the sampling system. The obtained samples are collected and blended in a mixer for homogenization treatment to produce a final specimen for analytical measurement. The homogeneous specimen is well accepted for its representative character.

A further object of this invention is to provide a set of facility for sampling of heterogeneous solid materials, comprising the elements: (a) a set of closed hood with glove, ventilation, and off-gas treatment system for sampling-machine accommodation, (b) a screw-drill sampling machine with an automatic control system for selection of the sampling depth and position, and (c) a support abutment of machine for positioning the container of the heterogeneous solid material. Multiple samples can be directly obtained from the closed container of the heterogeneous solid material either by manual or automatic operations of the sampling machine. The sampling number, depth, and position are predetermined and set by an automatic control system of the sampling machine.

Another object of this invention is to provide one set of portable screw-drill sampling machine using manual operation to obtain multiple samples following the procedure described above.

A further object of this invention is to provide a set of sampling method and facility for the heterogeneous solid materials. The system owns functions to prevent the radioactive powder from leakage whereby the regulations of radiation protection, environmental safety, and industrial safety are fully fulfilled.

Another object of this invention is to provide a set of sampling method and facility for the heterogeneous solid materials. The system can be operated at an open space for non-radioactive materials and the obtained sample owns representative character and is well recognized and accepted from the statistical point of view.

BRIEF DESCRIPTION OF THE INVENTION

The other objects and advantages of this invention can be clearly understood from the detailed description of a preferred embodiment and the accompanying drawings.

DETAILED DESCRIPTION OF THE INVENTION

Figure 1:
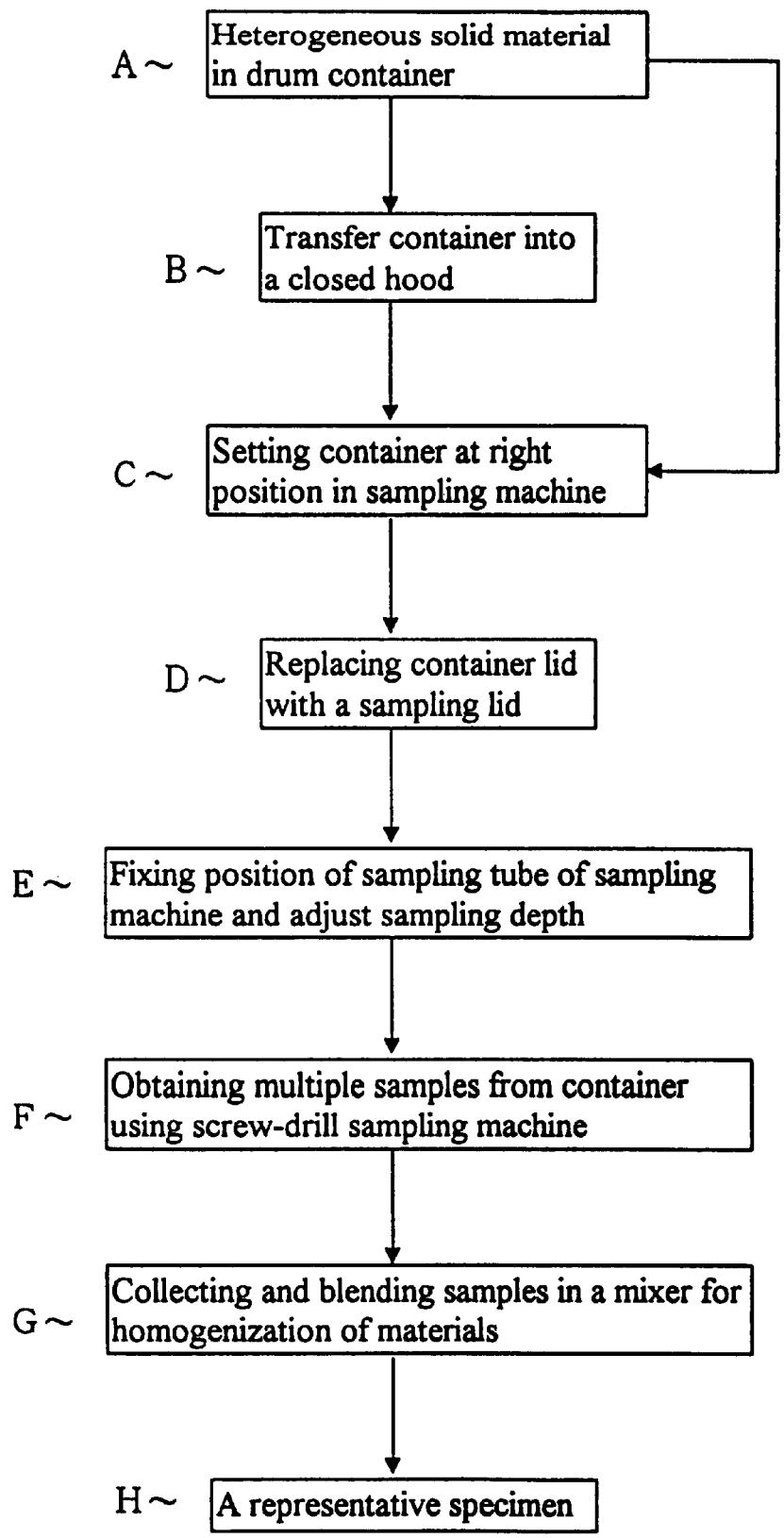
FIG. 1 shows a flow diagram of the present invention for sampling of the heterogeneous solid material.

Referring first to FIG. 1, a flow diagram of the present invention for sampling of the heterogeneous solid material is shown, in which block A shows the heterogeneous solid material, which is packed in a container A (e.g. 55-gallon drum) with a tight lid for easy transfer and transportation. Blocks B and C show two operation steps—transferring container A into a closed hood (step B) and setting the container A at the right position of the support abutment of a sampling machine (step C). In step D, the container lid is removed and replaced by a sampling lid. In step E, the position of sampling tube of the sampling machine is well fixed and the sampling depth is adjusted and then, the hood is tightly closed. In step F, multiple samples are sequentially obtained using the screw-drill sampling machine from the container. The sample number and position are preset and executed by the automatic control system. Either manual or automatic operations are achievable. Each sample is discharged to a sample bottle. In step G, samples are collected in a mixer for homogenization of materials using mixing and blending methods. Finally, a representative specimen, which is well accepted or recognized, is obtained in step H. After chemical analysis, the specimen composition (i.e. uranium content) can be effectively determined for account establishment of the uranium inventory.

The above cited flow diagram (process) is used for sampling of radioactive nuclear material, such as AUT. In order to fulfill the regulations of radiation protection, environmental protection and industrial safety, the operation must be proceeded in a closed hood. For non-radioactive materials, the sampling operation can be proceeded inside a room or at any open system. Hence, step B is not required and the hood is not closed in step E.

The sampling facility, essentially the screw-drill sampling machine, is designed and manufactured to execute the above stated sampling method. The following description illustrates the facility of the present invention.

Figure 3:
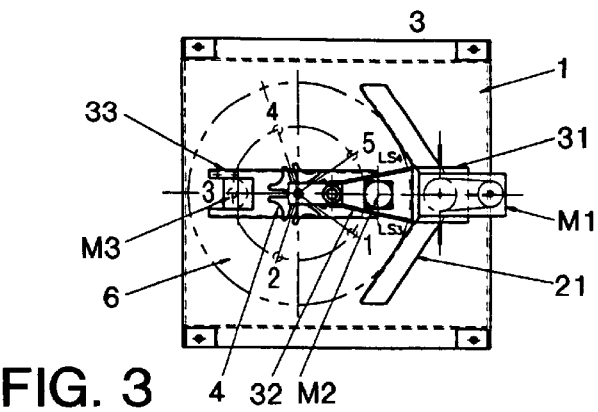
FIG. 3 is a top view drawing of the screw-drill sampling machine of the present invention.
Figure 4:
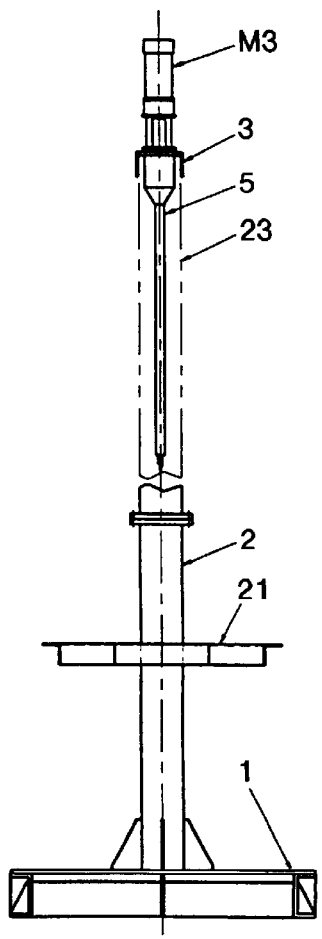
FIG. 4 is a sectional drawing from the front view of the screw-drill sampling machine.
Figure 2:
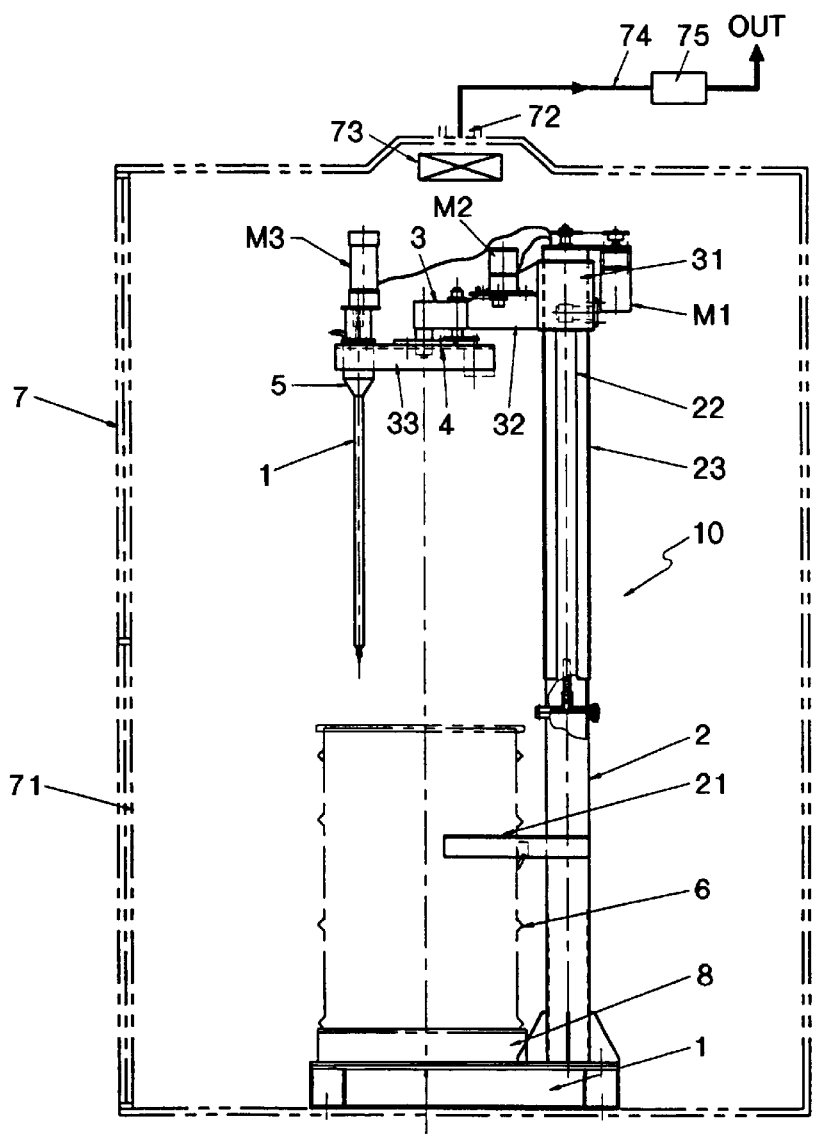
FIG. 2 is a side view drawing of the screw-drill sampling system of the present invention.

The screw-drill sampling machine 10, as shown from FIGS. 2 through 4, comprises: a support abutment of the machine 1, a supporter post 2 for connecting and supporting the suspension arm, a suspension arm set 3, a suspension arm motor M1 acting as a power supplier located at the top end of the post supporter 2 and used for longitudinal (up and down) slide movements of the suspension arm set 3 including suspension arms 3 and the screw-drill assembly, a Geneva indexer 4 located on the suspension arm set, a Geneva indexer Motor M2 supplying a power source for rotation of the Geneva indexer 4 following the programmed angle, a screw-drill sampling machine 5 located at the front end of the suspension arm set 3, and a motor M3 supplying a power source for operation of the screw-drill sampling machine 5.

The support abutment 1 consists of the square and circular steelwork made of steel plate and channel steel and is used to load the container 6 and an organic board (e.g. wood) 8. This support abutment 1 is preferably designed for loading the container so that the container transfer is easily done by an engine powered forklift. Near the bottom part of the post 2, one set of V-type arms 21 with an open front end is designed for off-position fixation of the material container 6. At the upper part of the post 2, one dovetailing for longitudinal movement of the system 22 is jointed and embedded into the upper part of the post 23. The suspension arm set 3 consists of a slide head 31, a slide arm 32, and a rotary arm 33. The suspension arm set 3 is sleeved to the upper part of the post 23 and embedded in the slide head 31 of the screw-drill machine system (not shown ). The longitudinal movement of the arm set 3 is directed by the dovetailing 22 and the whole arm system is supported by the post 2.

Figure 5:
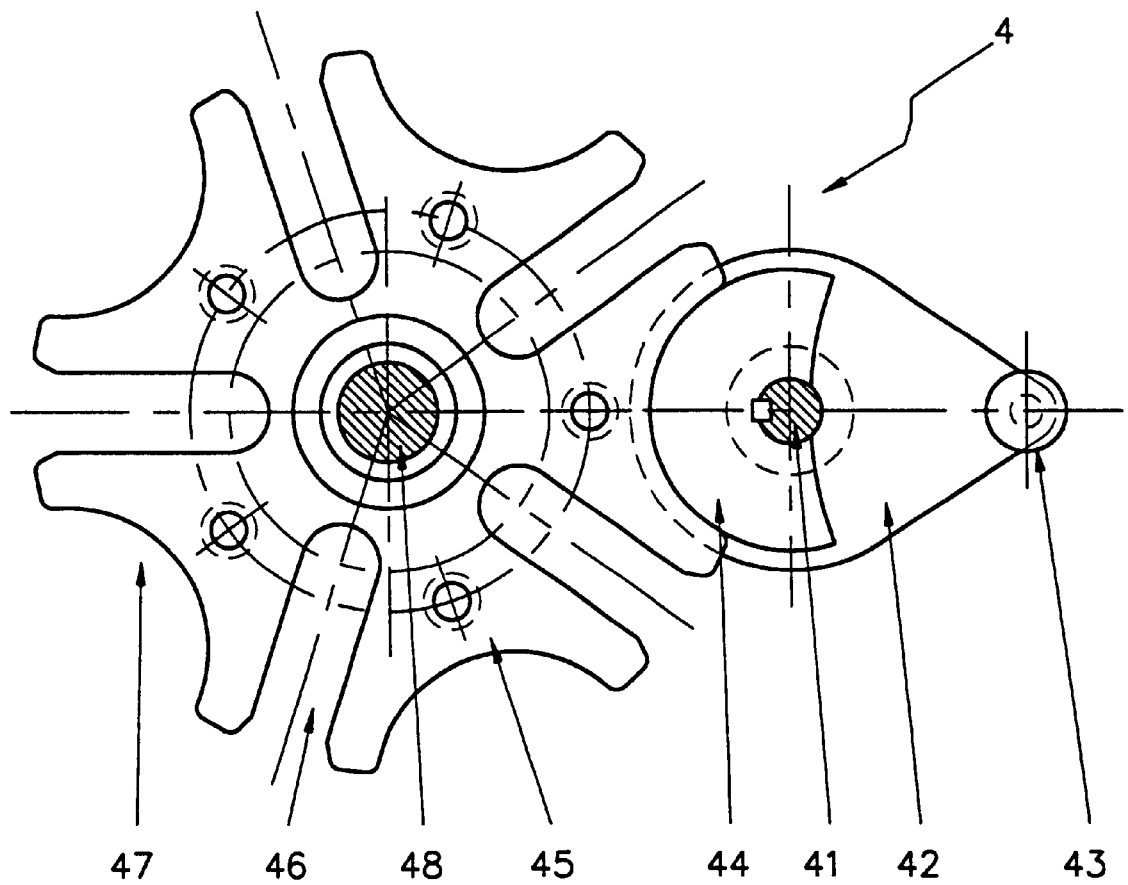
FIG. 5 shows a bottom view drawing of the 5-equiangular indexer of the present invention.

The Geneva indexer 4 is used to drive the rotary arm 33 of the screw-drill machine 5 to perform a sequential and stepwise rotation with fixed angular space around a center on the vertical axis. The indexer 4 consists of a familiar star shaped gear with male and female gear combination which provides the sequential and stepwise motion mechanism. An universal indexer is the best choice to give the arbitrary number of equal angular space on a horizontal circular plane by suitable adjustment so that the number of sampling point by the screw-drill machine can be controlled at one's own way. In this embodiment, an indexer with five equal angles is used. This demonstration is based on the case of an indexer of five equal angles, i.e. a 5-equiangular indexer. FIG. 5. shows the bottom-view drawing of the 5-equiangular indexer. This indexer 4 is located at the bottom part of the slide arm 32 and consists of a rotation pusher 42 with a fixed shaft 41, a roller 43, a cam 44, and a star gear 45 for intermittent system rotation guided by a fixed angle increment and operated by incorporation of the roller 43 and cam 44. In the present embodiment, since a 5-equiangular indexer is used, the star gear 45 is formed with five guide slots 46 and five arc dent parts 47 for engagement and rotation by the cam 44. Also, the star gear 45 rotates with the shaft 48 as the center.

Figure 6:
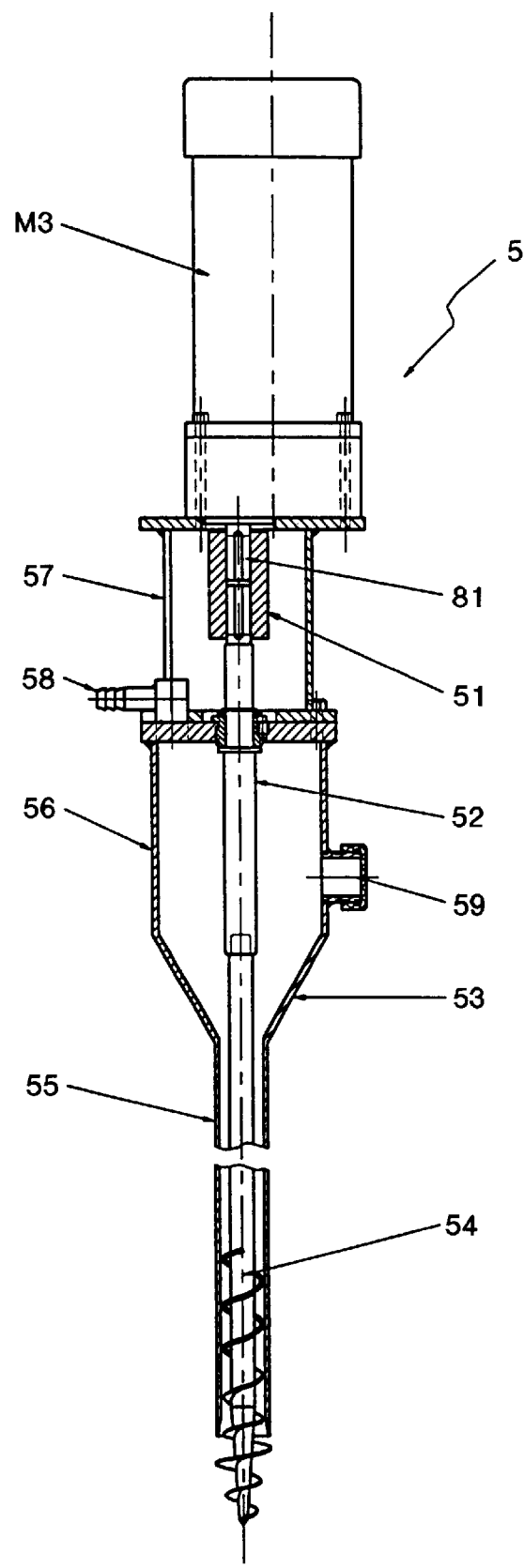
FIG. 6 shows a detailed structure of the screw-drill machine of the present invention.

The detailed structure of screw-drill sampling machine 5 is shown in FIG. 6. The machine 5 consists of a screw-drill shaft 52 connected to an output shaft 81 of a variable speed motor M3 by a coupler 51, an outer shell 56 with an upper part forming a hopper 53 capable of holding sampled material and a lower part forming a cylinder portion 55 enclosing screw-drill section 54 of the screw shaft 52 and an upper drum or motor support 57 connected to the above of the outer shell 56 for housing the coupler 51 and having the upper surface for placing thereon the motor M3. On top of the outer shell 56 is mounted a vent port 58 for off-gas discharge. And on the lateral side thereof is located a discharge port 59 for sampled material evacuation. The screw-drill shaft 52 preferably has two sections in a detachable way for easy replacement of the screw section 54.

In FIG. 2, the closed hood 7 is shown by imaginary line, which is used for sampling of the radioactive material in a closed system to confine any contamination of the material and protect the environment. A hood door 71 is adopted for transfer of the container 6 and material. A blower 73 and a ventilation port 72 are located at the top of the hood for off-gas discharge. The off-gas vented through a conduit 74 and is subjected to a clean treatment by an absolute filter 75 and finally discharged to the atmosphere. For non-radioactive and non-contaminated materials, the closed hood is not necessary for the sampling process. In addition, a view window and glove box (not shown in FIG. 2) are equipped in the hood 7 for operation from outside of the hood.

Figure 7:
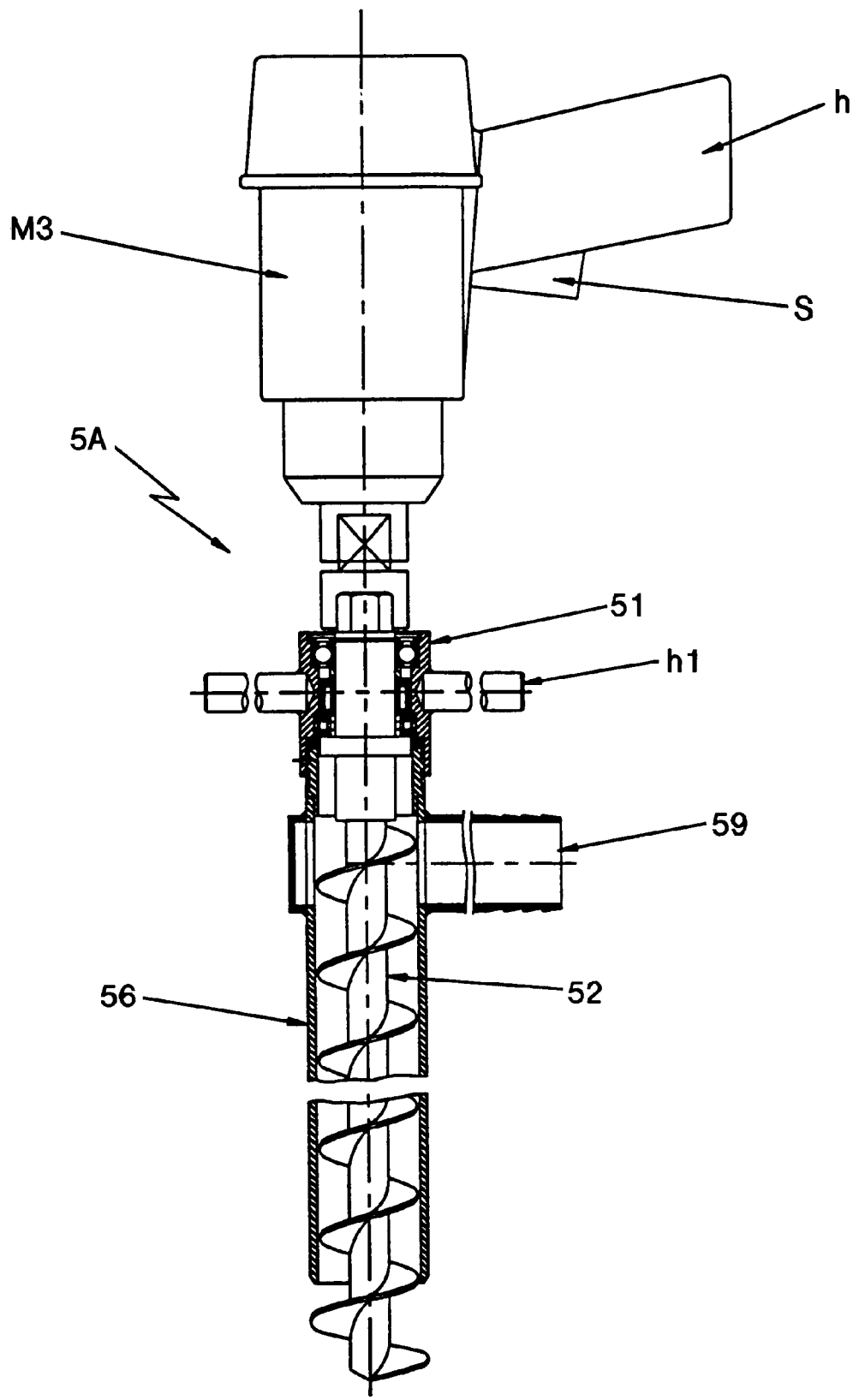
FIG. 7 shows a side-view section of a portable screw-drill assembly of the present invention.

FIG. 7. shows the partial side-view section of one embodiment of the portable screw-drill sampling assembly. For the embodiment described above, a fixed type set of screw-drill sampling system 10 is used and consists of an abutment 1, a supporter post 2, a suspension arm 3, the Geneva indexer 4, and the screw-drill sampling machine 5 for automatic sampling purpose. However, in the present embodiment, the sampling assembly is portable by hand and the sample is obtained by manual operation. The sampling assembly 5A is essentially equivalent to that of the sampling machine 5 described above and is designed for a local sampling operation with high mobility and convenience. The screw-drill sampling assembly 5A consists of hand holds h and h1, a motor M3 with a power switch S, a shaft connector 51, a screw shaft 52 and screw-drill shells 56 with a sample discharge port 59. This assembly can be directly operated by hand.

The operation procedure for sampling a material packed in a container by the screw-drill machine described above is extensively expounded by the following example.

The sampling operation of the radioactive material AUT following the mentioned automatic sampling procedure is demonstrated as an example. First, the door 71 of closed hood 7 is opened and the off-gas treatment system is started. The packed material 6 in container (e.g., 55 gallon steel drum) is transferred into the hood 7 using an engine powered forklift and fixed on the support abutment 1 of the sampling machine 10. Then, the container lid is replaced by a special cover with varied number of guided ports for sample drilling. The sampling position of the sampling tube 5 is selected and the sampling depth is adjusted. After that, the door of the closed hood 7 is closed and the ventilation system is started, whereby the sampling facility is ready for operation. Either by automatic or manual operations, AUT samples are sequentially obtained by screw drill machine following the preset path. Each sample retained in the screw-drill tube is discharged to a sampling bottle either through the discharged port 59 or through the shaft 52. In this example, five bottles of sample are obtained from each drum using a pentad equiangular indexer. Then, five samples are collected, mixed and blended in a closed container either by manual or electrical power mixing for material homogenization. Finally, one of the most representative or acceptable specimen is obtained from the homogenized powder. The said specimen is used for composition analysis or characterization. In this example, the uranium content is the key issue to be determined. Example:

The sampling process and facility according to the present invention was used to determine the uranium content of AUT of INER. The sample weights are in the range of 0.23~0.33 kg. Sampling can be operated using hood glove to prevent the radioactive powder from leakage and contamination. One of the most representative specimen, obtained from the homogenized powder generated by mixing and blending of the five samples, is used for chemical composition analysis. Analytical results show that the average uranium content is x=48.62(wt. %)(standard deviation, $\delta n=1.87$). However, that value obtained by the general method of random sampling is x=55.38(wt. %)(standard deviation, $\delta n=3.35$). The difference between these two values is 6.76 (wt. %) (about 13.9% in deviation), which is large enough to induce an argument. Now, this sampling method is well accepted by IAEA and INER. The statistical accuracy is also recognized. This example is employed to demonstrate the sampling procedure and facility for the radioactive material. However, a closed hood is not required if the material to be sampled is non-radioactive. For the portable screw-drill sampling machine 5A, the manual operation is good enough to complete the sampling task. Multiple samples can be also obtained one by one through the ports of a special drum cover by screw-drill assembly. Following the same procedure described above, the samples are collected in a container and homogenized by mixing and blending to obtain one of the most representative specimens. A programmable linear controller (PLC) is adopted for automatic operation of the screw-drill machine. The PLC system can control and memorize the sampling sequence (order), sampling point and execute the on-off action of the system. An adjustable limit switch is employed to control the pathway of the upward and downward movements of the sampling assembly and the sampling depth. A reversible, single phase AC motor with continuous speed variation is served as the sampling motor M3 to provide a suitable rotation speed for fitting the requirement of the material characteristics and discharging the sampled material from the sampling tube to a sampling bottle by reverse rotation of the motor. A controller for torque limit is set on the motor to keep the shaft in idle running if the torque exceeds the design value so that the sampling machine is well protected. Furthermore, the fixation of the container is achieved by a limit switch with contact sensor in connecting to a detector for alarm and fixation control. In addition to the indexer of fixed angular space or sampling number, an arbitrarily adjustable indexer for angle space variation or selection of sample number is best used to maximize the operation flexibility. An automatic control system is also used to achieve the automatic operation purpose. These technologies are well developed and easily applied to the sampling system.

Furthermore, the above container used for material package is not limited to the 55-gallon drum. Containers with diverse size and shape are suitable for sampling by this sampling machine using a proper lid (container cover). In addition to the radioactive material, any heterogeneous materials with agglomerate property, either used in the industrial or agricultural areas, can be effectively sampled by this method and facility. For a small container, the sample number may be reduced to one for each drum. However, more samples must be taken from different drums to obtain an acceptable specimen by mixing, blending, and homogenization of these samples.

The advantages of this sampling method and facility are described as follows:
1. Operation is executed in a closed hood through the gloves. The facility owns an automatic control system. These designs prevent the leakage of the radioactive material powder and reduce the dose acceptance of the operator. The regulations of radioactive material treatment and the principle of ALARA (As Low As Reasonably Achievable) are fulfilled.
2. One of the most representative/acceptable specimens can be effectively obtained by automatic fixations of the sampling position and depth as well as the selection of the sample number for the nuclear material packed inside a container.
3. The operation resistance for material sampling and, discharging by a screw-drill assembly can be reduced to a minimum value. The possibility of powder/dust generation is also minimized because the sampled material is confined inside the screw-drill tube.
4. The sample weight is well controlled for each operation to achieve a consistency of the sampling system.
5. The facility is compact and elaboration with flexibility and mobility. The only accessory facilities for operation are a closed hood and the off-gas treatment system.
6. Any heterogeneous material of a solid powder with agglomerated property can be sampled by this sampling system.
7. The representative specimen of a non-radioactive/non-poisonous material can be sampled at an open room without the equipment of a closed system.

The foregoing is a description of the preferred example of the invention and it is not intended that the invention be limited to the example shown. It may be apparent to those skilled in the art that various modifications, changes and substitutions may be made in such details without departing from the spirit and principles of the invention, the scope of which is defined in the appended claims.

What is claimed is:

1. A sampling assembly including a screw-drill machine for a container of heterogeneous solid material to be sampled, comprising:
   an abutment upon which a container of heterogeneous solid material to be sampled is adapted to be set,
   a supporter post on the abutment and including a fixation arm for locating the material container at a lower part of the post,
   a set of suspension arms including a rotary arm and a slide arm, the slide arm being vertically movable up and down along a guide device on an upper section of the post by a motor, the rotary arm being rotatable connected relative to and vertically movable with the slide arm, a Geneva indexer and a second motor for driving the Geneva indexer to intermittently horizontally rotate the rotary arm relative to the slide arm about a vertical axis, a screw-drill machine on the rotary arm, the screw-drill machine including a sampling tube and a screw that is adapted to be rotated in either one of a clockwise direction and a counterclockwise direction in the sampling tube, the screw-drill machine being longitudinally moved relative to the container by movement of the slide arm on the post by the first motor for sampling and discharging of material packed in the container, wherein rotation of the screw inside the sampling tube in one of a clockwise direction and a counterclockwise direction causes the material packed in the container to be one of drawn into and discharged from the sampling tube.

2. The assembly in accordance with claim 1, wherein the screw-drill sampling machine includes a reversible speed-variable motor, a screw-drill shaft connected to and driven together with an output shaft of the reversible speed-variable motor by a coupler, and the sampling tube includes an upper portion forming an expanded diameter sampled material-accommodating section and a lower portion forming a cylindrical protective sleeve section enclosing the screw-drill shaft, and wherein the screw-drill sampling machine includes a support drum disposed above the sampling tube and enclosing the coupler, the reversible speed-variable motor being mounted on an upper part of the support drum.

3. The assembly in accordance with claim 1, wherein the Geneva indexer includes a star gear and cam arranged to permit movement of the rotation arm and the screw-drill sampling machine between a plurality of different a sampling positions relative to the abutment.

4. The assembly in accordance with claim 1, wherein the Geneva indexer is arranged to permit one or more samples of the material in the container to be obtained from the container by the sampling assembly.

5. A sampling method for heterogeneous solid material from a container of heterogeneous solid material to be sampled, using a sampling assembly having a screw-drill machine, comprising the steps of:

setting the container, loaded with heterogeneous solid material, on an abutment of a screw-drill sampling machine;

replacing a container lid with a sampling lid;

obtaining more than two samples of material from different points within the container by using the sampling assembly to take the samples into a screw-drill tube of the sampling assembly;

transferring each sample of the more than two samples into one sample bottle from the screw-drill tube; and forming a homogenized sample for at least one of quality and quantity determination by mixing, blending, and homogenizing the more than two samples.

6. A sampling method in accordance with claim 5, wherein the method of sampling is performed in a closed hood equipped with a ventilation arrangement and an absolute filter for off-gas treatment.

7. A sampling method in accordance with claim 5, wherein the method of sampling heterogeneous material is performed inside a room in an open system.

8. A sampling method in accordance with claim 5, wherein the materials to be sampled are heterogeneous radioactive solid powders.

9. A sampling method in accordance with claim 5, wherein the materials to be sampled includes heterogeneous solid powders.

10. A sampling method in accordance with claim 8, wherein the materials to be sampled includes heterogeneous solid powders having an agglomerated character.

\* \* \* \* \*